(12) United States Patent
Mao (10) Patent No.: US 8,337,873 B2
(45) Date of Patent: Dec. 25, 2012

(54) HOLLOW AND POROUS ORTHOPAEDIC OR DENTAL IMPLANT THAT DELIVERS A BIOLOGICAL AGENT

(75) Inventor: Jeremy Jian Mao, Closter, NJ (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 1435 days.

(21) Appl. No.: 11/577,660

(22) PCT Filed: Oct. 20, 2005

(86) PCT No.: PCT/US2005/037948
§ 371 (c)(1),
(2), (4) Date: Jul. 20, 2007

(87) PCT Pub. No.: WO2006/047310
PCT Pub. Date: May 4, 2006

(65) Prior Publication Data
US 2008/0095815 A1 Apr. 24, 2008

Related U.S. Application Data

(60) Provisional application No. 60/621,575, filed on Oct. 22, 2004.

(51) Int. Cl.
*A61F 2/28* (2006.01)
*A61K 31/573* (2006.01)
*A61K 38/18* (2006.01)

(52) U.S. Cl. ...................... 424/422; 514/180; 623/23.51

(58) Field of Classification Search .................... None
See application file for complete search history.

(56) References Cited

U.S. PATENT DOCUMENTS

| | | | |
|---|---|---|---|
| 5,683,249 A | 11/1997 | Ibsen et al. | |
| 5,984,967 A * | 11/1999 | Zdeblick et al. | 623/17.16 |
| 6,053,916 A | 4/2000 | Moore | |
| 6,312,467 B1 | 11/2001 | McGee | |
| 6,949,251 B2 | 9/2005 | Dalal et al. | |
| 2003/0040790 A1* | 2/2003 | Furst | 623/1.11 |
| 2003/0148979 A1* | 8/2003 | Sosnowski et al. | 514/44 |
| 2003/0175410 A1 | 9/2003 | Campbell et al. | |
| 2003/0175656 A1 | 9/2003 | Livne et al. | |
| 2004/0013703 A1* | 1/2004 | Ralph et al. | 424/426 |
| 2004/0034357 A1 | 2/2004 | Beane et al. | |
| 2004/0138758 A1 | 7/2004 | Evans et al. | |
| 2004/0153154 A1 | 8/2004 | Dinkelacker | |
| 2004/0197311 A1 | 10/2004 | Brekke et al. | |
| 2004/0209228 A1 | 10/2004 | Ilan | |
| 2004/0210218 A1 | 10/2004 | Dixon | |
| 2005/0074877 A1 | 4/2005 | Mao | |

FOREIGN PATENT DOCUMENTS

WO   WO 0219337   3/2002

OTHER PUBLICATIONS

International Search Report issued in PCT/US2005/037948 (2006).
Alhadlaq et al., "Tissue-Engineered Neogenesis of Human-Shaped Mandibular Condyle from Rat Mesenchymal Stem Cells," *J. Dent. Res.*, 82: 951-956 (2003).
Alhadlaq et al., "Adult Stem Cell Driven Genesis of Human-Shaped Articular Condyle," *Ann. Biomed. Eng.*, 32 (7): 911-923 (2004).
Alhadlaq et al., "Mesenchymal Stem Cells: Isolation and Therapeutics," *Stem Cells and Development*, 13: 436-448 (2004).
Aubert-Pouessel et al., "In Vitro Study of GDNF Release from Biodegradable PLGA Microspheres," *J. Control Release*, 95: 463-475 (2004).
Baroli et al., "A Method to Protect Sensitive Molecules from a Light Induced Polymerizing Environment," *J. Pharm. Sci.*, 92 (6): 1186-1195 (2003).
Carrascosa et al., "Effect of Gamma-Sterilization Process on PLGA Microspheres Loaded with Insulin-Like Growth Factor-I (IGF-I)," *J. Biomater.*, 18: 95-108 (2003).
Carrascosa et al., "Microspheres Containing Insulin-Like Growth Factor I for Treatment of Chronic Neurodegeneration," *Biomaterials*, 25: 707-714 (2004).
Chin et al., "Differential Expression of Transforming Growth Factor-Beta Receptors I and II and Activation of Smad 3 in Keloid Fibroblasts," *Plast. Reconstr. Surg.*, 108 (2): 423-429 (2001).
Chong et al., "Rescue of Coronal Suture Fusion Using Transforming Growth Factor-Beta 3 (Tgf-Beta 3) in Rabbits with Delayed-Onset Craniosynostosis," *The Anatomical Record Part A*, 274A: 962-971 (2003).
Cleek et al., "Inhibition of Smooth Muscle Cell Growth in Vitro by an Antisense Oligodeoxynucleotide Release from Poly(DL-Lactic-Co-Glycolic Acid) Microparticles," *J. Biomed. Mater. Res.*, 35: 525-530 (1997).
Cleland et al., "Microsphere Formations Containing Recombinant Human Vascular Endothelial Growth Factor to Promote Local Angiogenesis," *J. Control Release*, 72 (1-3): 13-24 (2001).
Cohen et al., "Craniofacial Disorders Caused by Mutations in Homeobox Genes MSX1 and MSX2," *J. Craniofac. Genet. Dev. Biol.*, 20: 19-25 (2000).
Copland et al., "TGF-Beta 3 Expression During Umbilical Cord Development and Its Alteration in Pre-Eclampsia," *Placenta*, 23: 311-321 (2002).
Ding et al., "Determination of Water-Soluble Acid Distribution in Poly(Lactide-Co-Glycolide)," *J. Pharm. Sci.*, 93 (2): 322-331 (2004).
Elisseeff et al., "Controlled-Release of IGF-I and TGF-Beta 1 in a Photopolymerizing Hydrogel for Cartilate for Tissue Engineering," *J. Orthop. Res.*, 19: 1098-1104 (2001).
Ferguson et al., "Scar-Free Healing: From Embryonic Mechanisms to Adult Terapeutic Intervention," *Philos. Trans. R. Soc. Lond. B.*, 359: 839-850 (2004).
Garcia-Fuentes et al., "Design and Characterization of a New Drug Nanocarrier Made from Solid-Liquid Lipid Mixtures," *J. Colloid Interface Sci..*, 285: 590-598 (2005).

(Continued)

*Primary Examiner* — Shanon A Foley
(74) *Attorney, Agent, or Firm* — Barnes & Thornburg LLP; Alice O. Martin (57) ABSTRACT

This invention relates to the synthesis of new tooth or bone from an encapsulated biological agent such as a growth factor or stem cells contained within a hollow and porous biocompatible vehicle such as a titanium implant placed (implanted) within the body of a host animal such as a human.

16 Claims, 5 Drawing Sheets

OTHER PUBLICATIONS

Gombotz et al., "Stimulation of Bone Healing by Transforming Growth Factor-Beta 1 Released from Polymeric or Ceramic Implants," *J. Appl. Biomater.*, 5: 141-150 (1994).

Greenwald et al., "Regional Differentiation of Cranial Suture-Associated Dura Mater in Vivo and in Vitro: Implication for Suture Fusion and Patency," *J. Bone Mineral. Res..*, 15: 2413-2430 (2000).

Harris et al., "Mesenchymal Stem Cells Used for Rabbit Tendon Repair Can Form Ectopic Bone and Express Alkaline Phosphatase Activity in Constructs," *J. Orthop. Res.*, 22: 998-1003 (2004).

Hirshberg et al., "TGF-[Beta]3 in the Treatment of Pressure Ulcers: A Preliminary Report," *Adv. Skin Wound. Care*, 14 (2): 91-95 (2001).

Holland et al., "Advances in Drug Delivery for Articular Cartilage," *J. Control Release*, 86 (1): 1-14 (2003).

Hong et al., "Tissue-Engineering Rabbit Cranial Suture from Autologous Fibroblasts and BMP2," *J. Dent Res..*, 83 (10): 751-756 (2004).

Hosokawa et al., "TGF-Beta 3 Decreases Type I Collagen and Scarring After Labioplasty," *J. Dent Res..*, 82 (7): 558-564 (2003).

Jiang et al., "Biodegradable Poly(Lactic-Co-Glycolic Acid) Microparticles for Injectable Delivery of Vaccine Antigens," *Adv. Drug Deliv. Rev.*, 57: 391-410 (2005).

Kay et al., "Indirect Mitogenic Effect of Transforming Growth Factor-Beta on Cell Proliferation of Subconjunctival Fibroblasts," *Invest Ophthalmol. Vis. Sci*, 39 (3): 481-486 (1998).

Kohama et al., "TGF-Beta-3 Promotes Scarless Repair of Cleft Lip in Mouse Fetuses," *J. Dent. Res.*, 81 (10): 688-694 (2002).

Kojima et al., "Tissue-Engineered Trachea from Sheep Marrow Stromal Cells with Transforming Growth Factor Beta2 Released from Biodegradable Microspheres in a Nude Rat Recipient," *J. Thorac. Cardiovasc. Surg.*, 128 (1): 147-153 (2004).

Ksander et al., "Exogenous Transforming Growth Factor-Beta 2 Enhances Connective Tissue Formation and Wound Strength in Guinea Pig Dermal Wounds Healing by Secondary Intent," *Ann. Surg.*, 211 (3): 288-294 (1990).

Levine et al., "Spatial and Temporal Patterns of Immunoreactive Transforming Growth Factor Beta 1, Beta 2, and Beta 3 During Excisional Wound Repair" *Am. J. Pathol.*, 143 (2): 368-380 (1993).

Lewis et al., "Development of a Sustained-Release Biodegradable Polymer Delivery System for Site-Specific Delivery of Oligonucleotides: Characterization of P(LA-GA) Copolymer Microspheres in Vitro," *J. Drug Target.*, 5 (4): 291-302 (1998).

Lu et al., "TGF-[Beta]1 Release from Biodegradable Polymer Microparticles: Its Effects on Marrow Stromal Osteoblast Function," *J. Bone Joint Surg Am.*, 83-A(Suppl 1, Part 2): S1-82-S1-91 (2001).

Mao et al., "Growth and Development: Hereditary and Mechanical Modulations," *Am. J. Orthod. Dentofacial Orthop.*, 125 6): 676-689 (2004).

Mao, "Mechanobiology of Craniofacial Sutures," *J. Dent. Res.*, 81 (12): 810-816 (2002).

Martinez-Sancho et al., "Study of Gamm-Irradiation Effects on Aciclovir Poly(D,L-Lactic-Co-Glycolic) Acid Microspheres for Intravitreal Administration," *J. Control Release*, 99 (1): 41-52 (2004).

Midy et al., "Basic Fibroblast Growth Factor Adsorption and Release Properties of Calcium Phosphate," *J. Biomed. Mater. Res.*, 41: 405-411 (1998).

Mittal et al., "In Vitro Effects of Brain Derived Neurotrophic Factor Released from Microspheres," *Neuroreport.*, 5: 2577-2582 (1994).

Nicoll et al., "In Vitro Release Kinetics of Biologically Active-Transforming Growth Factor-Beta 1 from a Novel Porous Glass Carrier," *Biomaterials.*, 18: 853-859 (1997).

Oldham et al., "Biological Activity of rhBMP-2 Released from PLGA Microspheres," *J. Biomech. Eng.*, 122 (3): 289-292 (2000).

Opperman et al., "TGF-Beta 1, TGF-Beta 2, and TGF-Beta 3 Exhibit Distinct Patterns of Expression During Cranial Suture Formation and Obliteration in Vivo and in Vitro," *Journal of Bone and Mineral Research*, 12: 301-310 (1997).

Opperman et al., "Transforming Growth Factor-Beta 3 (Tgf-Beta3) in a Collagen Gel Delays Fusion of the Rat Posterior Interfrontal Suture in Vivo," *Anat. Rec.*, 267: 120-130 (2002).

Opperman et al., "Transforming Growth Factor-Beta3 (Tgf-Beta3) Down-Regulates Tgf-Beta3 Receptor Type I (Tbetar-1) During Rescue of Cranial Sutures from Osseous Obliteration," *Orthod. Craniofacial Res.*, 5: 5-16 (2002).

Pandit et al., "The Effect of TGF-Beta Delivered through a Collagen Scaffold on Wound Healing," *J. Invest. Surg.*, 12: 89-100 (1999).

Parker et al., "Release of Bioactive Transforming Growth Factor Beta(3) from Microtextured Polymer Surfaces in Vitro and in Vivo," *Tissue Eng.*, 8 (5): 853-861 (2002).

Peter et al., "Effects of Transforming Growth Factor Beta1 Released from Biodegradable Polymer Microparticles on Marrow Stromal Osteoblasts Cultured on Poly(Propylene Fumarate) Substrates," *J. Biomed. Mater. Res.*, 50 (3): 452-462 (2000).

Poisson et al., "Transforming Growth Factor-Beta Isoform Expression in the Perisutural Tissues of Craniosynostotic Rabbits," *Cleft Palate Craniofac. J.*, 41 (4): 392-402 (2004).

Prabaharan et al., "Chitosan-Based Particles as Controlled Drug Delivery Systems," *J. Drug Deliv.*, 12 (1): 41-57 (2004).

Richman et al., "Tooth Induction and Temporal Patterning in Palatal Epithelium of Fetal Mice," *Am. J. Anat.*, 175: 493-505 (1986).

Ruan et al., "Effects of Material Hydrophobicity on Physical Properties of Polymeric Microspheres formed by Double Emulsion Process," *J. Control Release*, 84 (3): 151-160 (2002).

Schiller et al., "TGF-Beta_Induced SMAD Signaling and Gene Regulation: Consequences for Extracellular Matrix Remodeling and Wound Healing," *Journal of Dermatological Science*, 35: 83-92 (2004).

Stafford et al., "Newer Insights into the Pathogenesis of Experimental Autoimmune Thyroiditis," *Intern. Rev. Immunol.*, 19: 501-533 (2000).

Verrecchia et al., "Transforming Growth Factor-Beta Signaling through the Smad Pathway: Role in Extracellular Matrix Gene Expression and Regulation," *J. Invest. Dermatol.*, 118 (2): 211-211 (2002).

Wei et al., "The Release Profiles and Bioactivity of Parathyroid Hormone from Poly(Lactic-Co-Glycolic Acid) Microspheres," *Biomaterials*, 25: 345-352 (2004).

\* cited by examiner

HOLLOW AND POROUS ORTHOPAEDIC OR DENTAL IMPLANT THAT DELIVERS A BIOLOGICAL AGENT

CROSS-REFERENCE TO RELATED PATENT APPLICATIONS

This application is a U.S. National Phase of International Patent Application No. PCT/US2005/037948 filed under 35 U.S.C. 37, filed Oct. 20, 2005, which claims the benefit of U.S. Provisional Patent Application No. 60/621,575, filed Oct. 22, 2004.

The government has certain rights in the invention (NIH DE015391 EB002332)

Biological agents are developed using orthopedic and dental implants as vehicles. A hollow and porous orthopedic or dental implant functions as a vehicle within which biological agents are loaded for their controlled release at a specific implanted location.

BACKGROUND OF THE INVENTION

In the United States, about 2 billion dollars are spent each year on orthopedic and dental implants. This correlates to about 700,000 orthopedic implant procedures performed in one year alone. As for dental implant procedures, about 69 percent of adults aged 35-44 years have lost at least one permanent tooth and, as such, are candidates for dental implants.

An implant, be it dental, orthopedic or other, is usually a biologically compatible material, like titanium, which is surgically inserted within the body to replace defective structures such as bone or teeth. Although these implants are becoming more commonplace, problems still remain in the area of osseointegration, both immediate and long-term. Most implant procedures focus mainly on mechanical repair without much thought as to regeneration of bone. It has been shown that the replacement of bones such as hip joints that initially osseointegrate properly deteriorate years later because of osteolysis at the bone to implant interface.

In order to lengthen the lifetime of implants and to accelerate the bone healing process, some research focuses on improving the initial anchorage of the implant as well as on preserving the strength of the bone to implant interface. However, none of these current approaches are satisfactory.

Transforming growth factor-$\beta 3$ is a member of a superfamily of cell mediators and plays fundamental roles in the regulation of cell proliferation and differentiation. In wound healing, TGF$\beta 3$ has been reported to attenuate type I collagen synthesis and reduce scar tissue formation. TGF$\beta 3$ has been reported to regulate the ossification of fibrous tissue in cranial sutures in craniosynostosis, a congenital disorder affecting 1 in approximately 2,500 live human births and manifesting as skull deformities, blindness, mental retardation, and death. During development, TGF$\beta 3$ regulates the adhesion of epithelial cells and subsequent fusion of the two palatal shelves, the failure of which leads to cleft palate. During umbilical cord development, TGF$\beta 3$ downregulation results in the commonly observed abnormal structure and mechanical properties of pre-eclampsia in umbilical cords, a leading cause of maternal and infant death during umbilical cord formation. TGF$\beta 3$ mediates the proliferation of corneal stromal fibroblasts by activating other endogenous factors, including FGF-2. The mechanism of fibrosis after glaucoma surgery is mediated by TGF$\beta 3$ and its effects on subconjunctival fibroblasts.

The fundamental roles of TGF$\beta 3$ in the development of a wide range of cells and tissues have prompted its adoption in tissue repair approaches. Topical application of TGF$\beta 3$ in gels was reported to ameliorate wound healing in patients at a dose of 2.5 μg/cm compared to placebo gels. Collagen gels soaked with TGF$\beta 3$ delivered to the ossifying cranial suture have been reported to delay its premature fusion. Bioactive TGF$\beta 3$ released from PLA microgrooved surfaces was reported to inhibit the proliferation of lung epithelial cells up to 24 hrs. Previous attempts for controlled release of cytokines include lipid nanoparticles, chitosan or gelatin-based particles collagen ceramics and porous glass. Although the short-term bioactivity of TGF$\beta 3$ has been investigated, exploration of prolonged release via microencapsulation is necessary for widespread needs to regulate cellular activities in the long-term during wound healing and tissue regeneration.

Despite previous efforts to investigate the therapeutic potential of TGF$\beta 3$, its effective use is limited by a number of common shortcomings such as short half life, instability in vivo, and relative inaccuracy of delivery systems.

SUMMARY

A hollow and porous implant is loaded with biologically active agents may be biological, pharmaceutical, herbal or chemical, such as stem cells and growth factors. These may be encapsulated, for example, in microspheres. A hollow and porous dental or orthopedic implant is loaded with one or more encapsulated biological agents that accelerates tooth or bone healing into and onto the implant after implantation. Loading is accomplished by procedures known in the art, taking care to contain the encapsulated biological agents in the implant, yet allow their release outside of the implant to host tissues and growth on and inside the implant. One way microspheres are loaded into biocompatible material is by vacuum. Stem cells and/or PLGA microspheres encapsulating growth factors are inserted into a scaffold such as a collagen sponge. The sponge is then packed into the hollow portion of the implant. Then the biocompatible materials are packed into the hollow core of the implant. The hollow and porous implant is made of a biocompatible solid material that adds load-bearing function to a defective bone or tooth, and yet is hollow and porous, thereby lowering the mechanical strength of the implant and reducing stress-shielding effects to the bone. Suitable materials for the hollow and porous implant include metal such as titanium. Osteoblasts may attach to the titanium and produce new bone. The hollow and porous implant can optionally have a coating on the metal. The cross section of the implant may be cylindrical, square, rectangular or irregular. The shape selected depends on the anatomical location and configuration of the tooth or bone to be repaired.

The encapsulated biological agents are loaded into the hollow and porous implant and promote the growth of new bone or tooth structures. The combination of porosity and controlled release techniques produce a new dental and/or orthopedic implant system that accelerates bone ingrowth and osseointegration (integration of, e.g. titanium into host bone or teeth). The controlled release technology delivers scheduled doses of growth factors and/or other chemical and/or pharmacological substances in a pre-defined temporal and spatial manner to promote bone in growth and/or osseointegration. The physical signs of the pores and hollow cylinder can be altered to optimize bone ingrowth and/or osseointegration. Suitable agents include growth factors and media specific to the growth or healing of new bone or teeth. Adult or embryonic stem cells may be added. The biologic agents act in the area of the implant, usually adjacent to it. Illustrative growth factors include the BMP family (2, 7, 8, 9), TGF~ family (1, 2, 3), ~FGF family, IGF family, VEGF, bFGF and mixtures of growth factors and chemical substances. Stem cells, when present, include endogenous adult mesenchymal stem cells. A suitable biocompatible vehicle is titanium and suitable encapsulating material is polymerized polylactic-co-glycolic acid.

Despite reports of roles in wound healing and tissue regeneration, long-term controlled release of TGFβ3 has not been demonstrated. A suitable composition for controlled release is TGFβ3 in poly-d-1-lactic-co-glycolic acid (PLGA) is encapsulated in microspheres. The release profiles of PLGA-encapsulated TGFβ3 with 50:50 and 75:25 PLA:PGA ratios differed throughout the analysis of bioactivity. To compare sterilization modalities of microspheres, bFGF was encapsulated in 50:50 PLGA microspheres and subjected to ethylene oxide (EO) gas, radio frequency glow discharge (RFGD) or ultra-violet (UV) light. The release of bFGF was significantly attenuated by UV light, but not significantly altered by either EO or RFGD. To verify its bioactivity, TGFβ3 (1.35 ng/ml) was control-released to the culture of human mesenchymal stem cells (hMSCs) under induced osteogenic differentiation. Alkaline phosphatase staining intensity was markedly reduced 1 wk after exposing hMSC-derived osteogenic cells to TGFβ3. This was confirmed by lower alkaline phosphatase activity ($2.25 \pm 0.57$ mU/ml/ng DNA) than controls (TGFβ3 free) at $5.8 \pm 10.9$ mU/ml/ng DNA ($P<0.05$). Control-released TGFβ3 bioactivity was further confirmed by lack of significant differences in alkaline phosphatase upon direct addition of 1.35 ng/ml TGFβ3 to cell culture ($p>0.05$). Microencapsulated TGFβ3 is useful in wound healing and tissue engineering applications.

TGFβ3 was encapsulated in PLGA microspheres, its release kinetics were determined and the bioactivity of control-released TGFβ3 on osteogenic differentiation of human mesenchymal stem cells (hMSCs) was investigated. The effects of several commonly used sterilization methods on the morphology of PLGA microspheres and the release kinetics of encapsulated growth factor were determined. These include ultraviolet light, ethylene oxide gas, and radio frequency glow discharge, and were designed to aid in the choice of sterilization modality in subsequent in vivo studies using PLGA microspheres encapsulating various growth factors.

Hollow and porous implants may be biologically engineered in any shape or size as long as they are capable of incorporating growth factors and/or adult mesenchymal stem cells. Immunorejection issues are minimized by using bone-forming cells from the patient's own bone marrow.

New bone is integrated with the patient's own tissues as a biologically driven healing process. Orthopedic surgical approaches to place the implant are known in the art and can be utilized without requiring separate human subjects approval process.

BRIEF DESCRIPTION OF THE DRAWINGS

FIG. 1 is a series of three photographs (FIG. 1A, FIG. 1B and FIG. 1C) that illustrate titanium implants. The implants were smooth, hollow and porous cylindrical titanium rods measuring 4 mm×2 mm×6 mm (outer diameter×inner diameter×length) containing four cross-holes measuring 1 mm in diameter. A: Dental implant commercially available from NobelBioCare under the name Steri-Oss™. B: Dental implant commercially available from Straumann under the name ITITM. C: Custom-made hollow and porous titanium implant which mimics the dimensions of commercially available implants.

FIG. 2A: PLGA microspheres with diameter of about 64~16 pm and encapsulating TGF-~I. The bar in the photo is about 100 p. FIG. 2B: Graph illustrating in vitro release profile for microspheres loaded with TGF-~1. TGF-~1 is released in a quick burst of about 0.2 0.05 ng in 3 days and sustains release up to 4 weeks.

FIG. 3A: PLGA microspheres were injected into a collagen sponge in preparation for in vitro studies. FIG. 3B: In vitro studies showed an increase in the DNA content within the collagen sponges at 3 weeks suggesting an increased number of cells that migrated into microsphere loaded implants.

DETAILED DESCRIPTION

A hollow and porous orthopedic or dental implant is loaded by methods known to those of skill in the art with one or more encapsulated biological agents for release within or on a human body. The encapsulated biological agents are loaded in the hollow core and accelerate tooth or bone healing adjacent to the implant after implantation. The biological agents may diffuse or otherwise travel through the encapsulating cell membrane, or the encapsulating structure ruptures to provide release of the biological agents, or both occur such that the biological agents traverse through the porous implant and into the surrounding tissue.

A hollow and porous implant containing an encapsulated biological agent includes a growth factor that can be provided alone or in addition to embryonic or adult stem cells, for example, adult mesenchymal stem cells (MSCs). MSCs can be prepared from bone marrow cells or other sources such as adipose tissue or peripheral blood. Use of endogenous cells minimizes risk of immunorejection.

Exemplary growth factors include the BMP family, for example those factors designated BMP-2, BMP-7, BMP-8 and BMP-9 (also referred to as BMP 2, 7, 8, and 9), the TGFβ family that includes those molecules referred to as TGF-~1, TGF~2 and TGF~3 (also referred to as TGFβ1, 2, and 3), the FGF family, the IGF family, VEGF, bFGF, other growth factors, and mixtures of two or more of the above or other growth factors.

Stem cells such as embryonic or adult stem cells contain growth factors and are surrounded by a cell membrane that encapsulates the growth factors. These cells can be obtained from bone marrow, adipose tissue and peripheral blood, as well as from other sources. Adult mesenchymal stem cells (MSCs), fetal stem cells or other adult stem cells can be used. Adult mesenchymal cells are derived from bone marrow cells that can differentiate into osteocytes.

Adult MSCs are capable of differentiating into all connective tissue-forming cell lineages including cartilaginous, osseous, and adipose tissues. MSCs can be obtained with minimally invasive procedures from bone marrow or other connective tissue sources in the body, are highly expandable in culture, and can be readily induced to differentiate after exposure to well-established inducing supplements. Moreover, the use of the adult stem cells is advantageous over the use of embryonic stem cells for ethical reasons.

Figure 1:
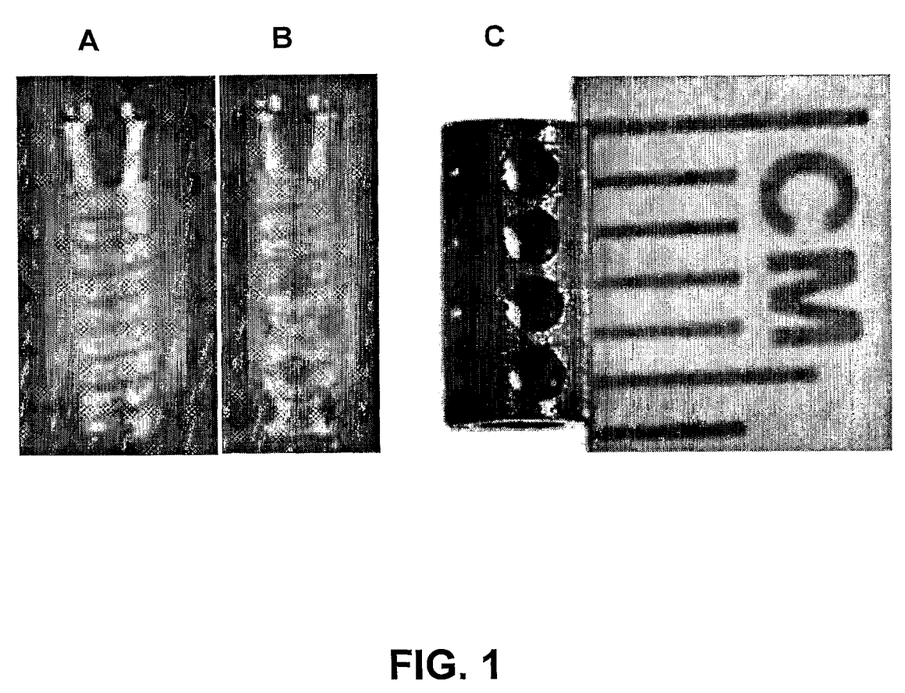

The hollow and porous implant is constructed from a biocompatible solid material, e.g. made of one or more metals, such as stainless steel or titanium (FIG. 1).

The shape of the hollow and porous implant is programmed as needed. The shape of the implant may resemble a bone, or is cylindrical, or other as needed. The implant is porous or foraminous (has one or more holes that penetrate a wall of the implant to permit transfer of cells, proteins and smaller molecules from the inside to the outside of the implant and vice versa). That is, the surface of an implant defines spaces that permit entrance and egress of liquid and proteins into and out of the hollow and porous implant. The hollow and porous implant may resemble a metal mesh. The wall-penetrating holes need not directly traverse the implant wall, but can take a meandering path.

The hollow and porous implant may contain a second biocompatible material inside and may also have a coating of a second biocompatible material such as a hydrogel polymer. Hydrogel polymers provide bone-forming cells with an environment mimicking the extracellular matrix in the body.

Hydrogel polymers are hydrophilic, three-dimensional networks that absorb large amounts of water or biological fluids while maintaining their distinct three-dimensional structure. The coating may be a photopolarizable hydrogel polymer, or hydrated polylactic-co-glycolic acid.

Polylactic-co-glycolic acid-based hydrogel polymers have certain advantages for biological applications because of their proven biocompatibility and their demonstrated capacity to support growth and differentiation of MSCs into multiple lineages such as bone. These polymers assist maintaining microspheres within the implant. Also, the administration of the cell-polymer system under the skin with a minimally invasive procedure (injection) and the ability of these hydrogels to undergo transdermal photopolymerization are advantageous in biological systems.

The hollow and porous implant is loaded with one or more biological agents such as embryonic or adult mesenchymal stem cells and/or one or more growth factors encapsulated within a hydrogel polymer, or both. The encapsulating hydrogel may be a material that is typically polylactic acid, polyglycolic acid, polyethylene glycol, polyethylene glycol and mixtures thereof. The hydrogel preferably includes polylactic-co-glycolic acid which has been polymerized by the action of ultraviolet light and a photoinitiator such as 2-hydroxy-1-[4-(hydroxyethoxy)phenyl]-2-methyl-1-propanone.

Figure 2:
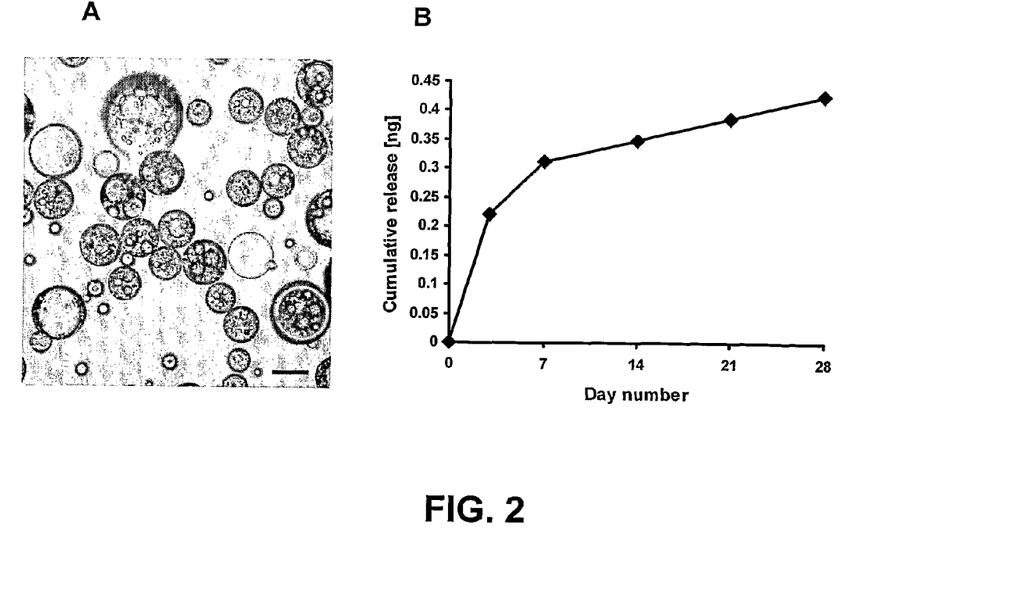
FIG. 2 is a photograph (FIG. 2A) and graph (FIG. 2B) that illustrate polylactic-co-glycolic acid (PLGA) microspheres fabricated in the laboratory using an oil-water-oil double emulsion technique and their use.

Long-term delivery via controlled release offers a way to circumvent previous limitations associated with instantaneous application of TGFβ3, for example, in collagen scaffolds. One approach of controlled release is by encapsulating peptides and proteins in microspheres (FIG. 2). Poly-d-1-lactic-co-glycolic acid (PLGA) is degraded by hydrolysis into biocompatible byproducts including lactic and glycolic acid monomers. Lactic and glycolic acids are eliminated in vivo as $CO_2$ and $H_2O$ via the Krebs cycle, eliciting minimal immune response. PLGA microspheres are fabricated using the double-emulsion-solvent-extraction technique, which allows the control of sphere diameter and degradation kinetics, while maintaining the stability and bioactivity of the encapsulated growth factors. The encapsulation and release kinetics of several growth factors such as BMPs, TGFβ1 and 2, neurotrophic growth factors, VEGF, and IGFs have been reported. However, microencapsulation of TGFβ3 and its release kinetics is unknown. The other two mammalian isoforms, TGFβ1 and TGFβ2, promote cranial suture fusion and osteogenesis. TGFβ1 has been shown to enhance the proliferation and osteoblastic differentiation of marrow stromal cells cultured on poly(propylene fumarate) substrates. TGFβ1 and 2 are continuously present during the osseous obliteration of the frontonasal suture of the rat. TGFβ3, in contrast, is associated with the maintenance of the rat coronal suture unossified state.

Figure 3:
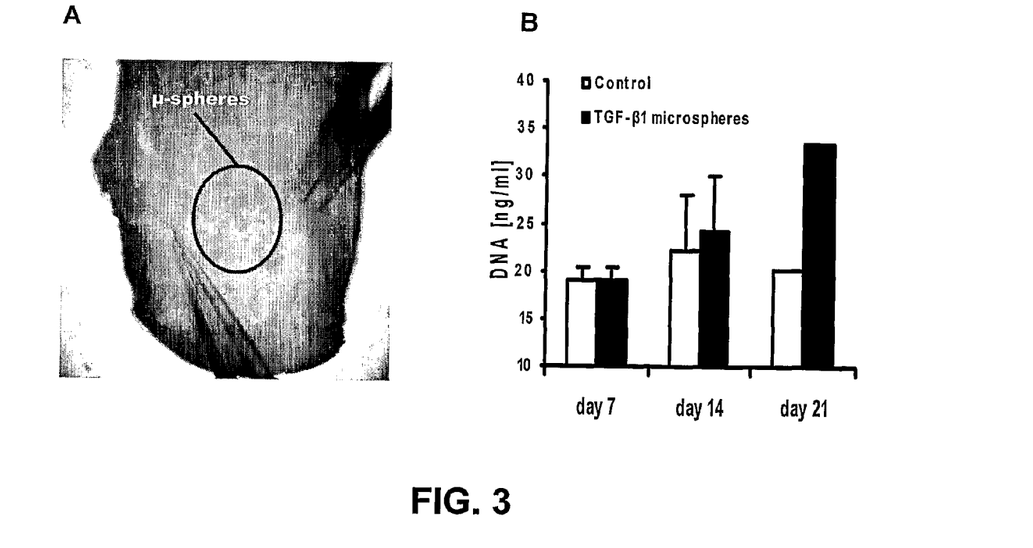
FIG. 3 is a photograph (FIG. 3A) and graph (FIG. 3B) that show PLGA microspheres and the results of their usage.

The encapsulated biological agent is present within a biological matrix that may include a natural material comprised of alginate, sponge, chitosan, coral, agarose, fibrin, collagen, bone, silicone, cartilage, hydroxyapatite, calcium phosphate, and mixtures thereof. A collagen sponge may be used to carry encapsulated growth factors or stem cells or both within the hollow and porous implant (FIG. 3). Hydrogel polymers may also be used as a biological matrix.

In addition, the biological matrix may include an osteogenic agent, for example dexamethasone. Additional exemplary osteogenic agents include one or more members of the bone morphogenetic protein family, the transforming growth factor protein family, and the vascular endothelial growth factor protein family, and mixtures of such osteogenic agents. The biological matrix may further include a nutrient medium.

A composition may be in the shape of a partial or entire bone in a titanium vehicle; a biological matrix; an osteogenic agent; a nutrient medium; at least one antibiotic; and adult mesenchymal stem cells, wherein the titanium vehicle provides a solid support for the biological matrix that holds the osteogenic agent, medium, antibiotic and cells.

A composition may be in the shape of a cylinder or a partial or entire bone that is composed of a titanium vehicle; a hydrogel comprising polylactic-co-glycolic acid and 2-hydroxy-1-[4-(hydroxyethoxy)phenyl]-2-methyl-1-propanone; osteogenic agents including dexamethasone and transforming growth factor beta-1; a nutrient medium including beta-glycerophosphate and ascorbic acid 2-phosphate; penicillin; streptomycin; and adult mesenchymal stem cells derived from human bone marrow wherein the titanium vehicle serves as a solid support for the hydrogel that holds the osteogenic agents, medium, antibiotics and cells.

A method of producing an osteochondral construct includes the steps of providing adult or embryonic stem cells such as adult mesenchymal stem cells from bone marrow; treating the cells with osteogenic media to induce differentiation into osteoblasts; and loading the osteoblasts onto a biocompatible vehicle comprised of titanium mesh and a hydrogel matrix. Suitable osteogenic media is any used in the art to initiate or promote bone growth. Endogenous bone marrow minimizes rejection.

A method of producing a biologically engineered partial or entire bone in vivo includes implanting a composition of a biocompatible titanium vehicle with a hydrogel coating and a sample of adult or embryonic stem cells such as adult mesenchymal stem cells into a host animal. Illustrative host animals include laboratory animals such as rat, mouse and rabbit, a companion animal such as a dog or cat, a veterinary animal such as a horse (equine), cow (bovine), sheep (ovine) or goat (caprine), or an primate such as a monkey, ape (chimp, orangutan or gorilla) or man (humans).

A method for inducing growth of new bone or tooth at the site of an implant includes the steps of (a) providing an implant of a hollow and porous biocompatible vehicle containing a biological matrix admixed with osteocytes, (b) implanting that implant into a host animal (e.g. a patient); and (c) maintaining the animal (e.g. a patient) for a time period sufficient for the bone or tooth to grow. Illustratively, stem cells such as adult mesenchymal stem cells are harvested. Those cells are treated with an osteogenic medium to induce differentiation into osteocytes. The osteocytes so prepared are loaded into a hollow and porous perforated titanium vehicle having a hydrogel matrix to form an admixture with the matrix. The implant is implanted into a patient. That patient is maintained as medically (dentally) appropriate for a time sufficient for new cells to grow.

The use of the article "a" or "an" is intended to include one or more.

EXAMPLES

Example 1

Sustained Release of TGFβ3 from PLGA Microspheres and its Effects on Early Osteogenic Differentiation of Human Mesenchymal Stem Cells Preparation of PLGA Microspheres and Encapsulation of TGFβ3

Microspheres of poly(DL-lactic-co-glycolic acid) (PLGA; Sigma, St. Louis, Mo.) of 50:50 and 75:25 PLA:PGA ratios (Sigma, St. Louis, Mo.) were prepared using double emulsion technique ((water-in-oil)-in-water). (Lu, L., et al, 2001; Wei G, et al, 2004; Ruan, G, et al, 2002) A total of 250 mg PLGA was dissolved into 1 ml dichloromethane. A total of 2.5 µg of recombinant human TGFβ3 with molecular weight of 25 kDa (R&D Systems, Minneapolis, Minn.) was diluted in 50 µl of reconstituting solution per manufacturer protocol and added to the PLGA solution, forming a mixture (primary emulsion) that was emulsified for 1 min (water-in-oil). The primary emulsion was then added to 2 ml of 1% polyvinyl alcohol (PVA, MW 30,000-70,000), followed by 1 min mixing ((water-in-oil)-in-water). Upon adding 100 ml PVA solution, the mixture was stirred for 1 min. A total of 100 ml of 2% isopropanol was added to the final emulsion and continuously stirred for 2 hrs under chemical hood to remove the solvent. Control microspheres (empty and without TGFβ3) were fabricated using the same procedures with the exception of using 50 µl distilled water instead of TGFβ3 solution. (Cleek R L, et al, 1997) Empty microspheres containing only water as controls were implemented to subtract the possible effects of degradation byproducts of PLGA alone. PLGA microspheres containing TGFβ3 or distilled water were isolated using filtration (2 µm filter) and washed with distilled water. Microspheres were frozen in liquid nitrogen for 30 min and lyophilized for 48 hrs. Freeze-dried PLGA microspheres were stored at −20° C. prior to use.

Sterilization of PLGA Microspheres

Microspheres were sterilized prior to in vivo use in wound healing and regenerative medicine. In order to determine the efficacy of several commonly used sterilization techniques, basic fibroblast growth factor (bFGF) was encapsulated in PLGA microspheres with 50:50 PLA:PGA ratio using the same technique as described herein. The rationale for using bFGF instead of TGFβ3 was that bFGF costs less than TGFβ3, and has similar structural properties. Although the solubility properties of bFGF may differ from TGFβ3, resulting in different encapsulation efficiencies and release kinetics, the effects of sterilization on polymer structural changes following sterilization may be comparable. The fabricated bFGF-encapsulating PLGA microspheres were randomly divided into 3 groups: 1) placed under ultra-violet light (UV) for 30 min (n=3), 2) exposed to ethylene oxide gas (EO) for 24 hrs (n=3), or 3) exposed to radio frequency glow discharge (RFGD) for 4 min at 100 W (n=3). Four hours following the 3 sterilization modalities, scanning electron microscopy (SEM) was used to determine the surface morphology of bFGF-encapsulating PLGA microspheres. In addition, immediately after all 3 sterilization modalities, 10 mg of bFGF-encapsulating PLGA microspheres were separately weighed and immersed in 1 ml of 1% BSA solution in water bath at 60 rpm and 37° C. to determine bFGF release kinetics. Supernatants were fully collected at Days 7, 14, 21, and 28 after centrifuging at 5000 rpm for 10 min. After each collection, fresh 1 ml of 1% BSA was added to microspheres. Release kinetics was measured using a bFGF enzyme-linked immunosorbent assay kit (bFGF ELISA; R&D Systems, Minneapolis, Minn.).

In Vitro TGFβ3 Release Kinetics

After freeze-drying, the actual amount of encapsulated TGFβ3 per ml in units of mg of PLGA microspheres was detected using an enzyme-linked immunosorbent assay kit (TGFβ3 ELISA; R&D Systems, Minneapolis, Minn.) in the hydrophilic extraction of the dissolved PLGA microspheres. A total of 10 mg TGFβ3-encapsulating PLGA microspheres were dispersed in 1 ml of 1% BSA solution, and continuously agitated in water bath at 60 rpm and 37° C. (n=3). The entire amount of supernatants was collected periodically and amount of TGFβ3 was quantitatively measured using the TGFβ3 ELISA kit for each sample. The TGFβ3 release rate was expressed as a percentage of the total TGFβ3 per mg PLGA microspheres. Entrapment yield was determined by dissolving 10 mg of TGFβ3 encapsulating PLGA microspheres in 1 ml of chloroform and adding 1 ml of 1% BSA solution (n=3). Mixtures were allowed to settle for 6 hrs and TGFβ3 rich solution was collected for quantification of amount encapsulated using ELISA. PLGA microspheres encapsulating TGFβ3 were imaged with SEM on Day 4 of exposure to aqueous solution to observe surface morphology.
Culture and Osteogenic Differentiation of Human Mesenchymal Stem Cells Human mesenchymal stem cells (hMSCs) were isolated from the bone marrow of an anonymous healthy donor (All-Cells, Berkeley, Calif.), culture-expanded in 6-well plates at a density of 30,000 cells/well. (Alhadlaq, A., et al, 2004; Alhadlaq, A., and Mao, 2004) Monolayer hMSC cultures were maintained at 37° C., 95% humidity, and 5% $CO_2$, using Dulbecco's Modified Eagle's Medium (DMEM-c; Sigma, St. Louis, Mo.) supplemented with 10% fetal bovine serum (FBS; Atlanta Biologicals, Norcross, Ga.), and 1% antibiotic and antimycotic (10,000 U/ml penicillin (base), 10,000 μg/ml streptomycin (base), 25 μg/ml amphotericin B) (Atlanta Biologicals, Norcross, Ga.). Media were changed every 3 to 4 days. Human MSCs were differentiated into osteogenic cells with osteogenic supplements containing 100 nM dexamethasone, 50 μg/ml ascorbic acid and 100 mM β-glycerophosphate. MSCs treated with the osteogenic supplements begin to differentiate into osteoblast-like cells that expressed multiple osteoblast markers. The early osteogenic potential of hMSC-derived cells was evaluated by alkaline phosphatase (ALP) staining and quantification using enzyme reagent. (Alhdlaq, A., et al, 2004; Alhadlaq, A., and Mao, 2004; Alhadlaq, A., Mao, J. J., 2003).
Bioactivity of Control-Released TGFβ3 on Osteogenic Differentiation of Human Mesenchymal Stem Cells Ethylene oxide gas sterilized 50:50 co-polymer ratio TGFβ3-encapsulating PLGA microspheres (62.5 mg yielding 1.35 ng TGFβ3 per 2 ml of medium in 7 days, estimated from release kinetics, FIG. 7) were placed in transwell inserts (0.4 μm pore size) (Becton Dickinson Labware, Franklin Lakes, N.J.) (Lu, L., et al, 2001). The transwell inserts with microspheres were placed in cell culture wells, approximately 0.9 mm above the monolayer culture of undifferentiated hMSCs, exposing the cells to released TGFβ3 without direct contact with PLGA microspheres. At this time, osteogenic supplemented DMEM medium was added (n=3). In the control group, 0 or 1.35 ng/ml TGFβ3 solution without microsphere encapsulation was added along with osteogenic supplemented medium to monolayer culture of hMSCs (n=3). Osteogenic supplemented medium was changed at day 3. Fresh TGFβ3 in solution was added for the control group at media change. ALP activity of hMSC-derived osteogenic cells exposed to TGFβ3 in solution (without microsphere encapsulation) was measured after 7 days and compared to the ALP activity of hMSC-derived osteogenic cells exposed to the same-dosed TGFβ3 (1.35 ng/ml) released from PLGA microspheres (n=3). The TGFβ3 release amount obtained above was estimated from the amount of TGFβ3 released from 62.5 mg PLGA microspheres over the initial 7 days. Alkaline phosphatase activity was measured using ALP Reagent (Raichem, San Diego, Calif.) and normalized to DNA content of hMSC-derived osteogenic cells. DNA content was measured using fluorescent DNA quantification kit (BioRad Labs, Hercules, Calif.) (Alhdlaq, A., et al, 2004).

Statistical Analysis

Figure 4:
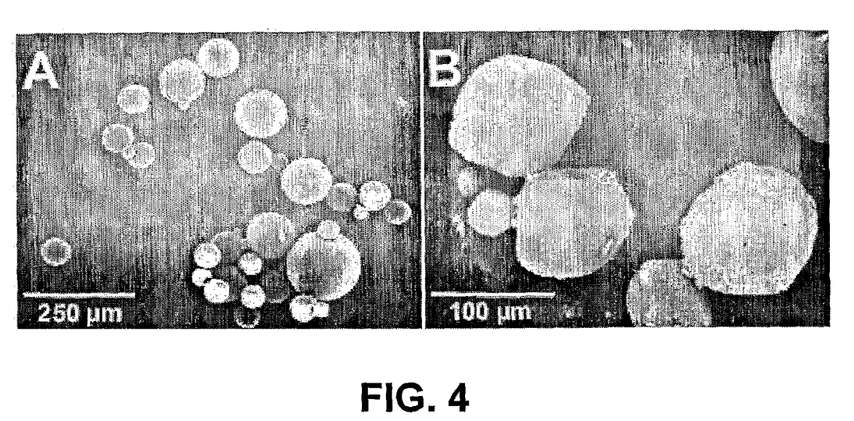
FIG. 4. relates fabrication and degradation of PLGA microspheres. A: Representative SEM image of microspheres fabricated from poly-d-1-lactic-co-glycolic acid (PLGA) with 50:50 PLA:PGA ratio with encapsulated TGFβ3; the average diameter of TGFβ3-encapsulating PLGA microspheres was $108 \pm 62$ μm. B: Representative SEM image of anticipated degradation of TGFβ3-encapsulating PLGA microspheres in PBS solution after 4 days.
Figure 5:
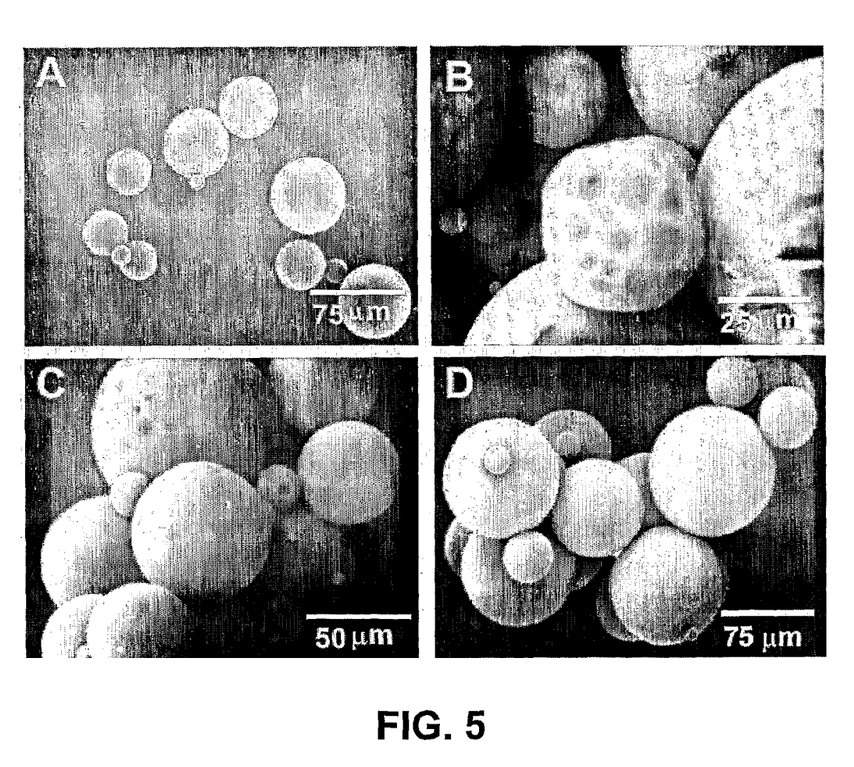
FIG. 5. shows morphological changes of sterilized PLGA microspheres under SEM. A: Un-sterilized PLGA microspheres. B: Ultra-violet light (UV) sterilized PLGA microspheres (30 min) showing severe detrimental effect of UV sterilization. C: Ethylene oxide (EO) gas sterilized PLGA microspheres for 24 hrs. D: Radio frequency glow discharge (RFGD)-sterilized PLGA microspheres (4 min, 100 W). In contrast to severe surface degradation changes induced by UV light, EO gas and RFGD did not yield marked surface degradation of PLGA microspheres.

Student T tests and ANOVA were used to compare the release rates of bFGF-encapsulating PLGA microspheres after different sterilization modalities, TGFβ3 release rates between 50:50 and 75:25 PLA:PGA ratios, and ALP activity of hMSC-derived osteogenic cells between control group (TGFβ3 free) and two experimental groups (release from PLGA microspheres or directly added to cell culture medium). All statistical analyses were performed with an α level of 0.05 using Minitab 14 software (State College, Pa.).
TGFβ3 Encapsulated in PLGA Microspheres TGFβ3-encapsulating PLGA microspheres prepared by double-emulsion-solvent-extraction technique showed spherical shape and smooth surface for the two compositions of PLGA (FIG. 4A). The average diameter of TGFβ3-encapsulating PLGA microspheres was 108±62 μm (FIG. 4A). Upon emersion in aqueous solution for 4 days, PLGA microspheres apparently began surface degradation (FIG. 4B).
Sterilization of PLGA Microspheres and bFGF Release Kinetics Different sterilization methods for PLGA microspheres had different effects on their surface degradation by SEM. PLGA microspheres sterilized with UV light showed marked surface deleterious effects (FIG. 5B) in comparison with un-sterilized PLGA microspheres (FIG. 5A). In contrast, ethylene oxide (EO) gas and radio frequency glow discharge (RFGD) appeared to induce minimal morphological changes on the surface degradation of PLGA microspheres (FIGS. 5C and 5D).

Figure 6:
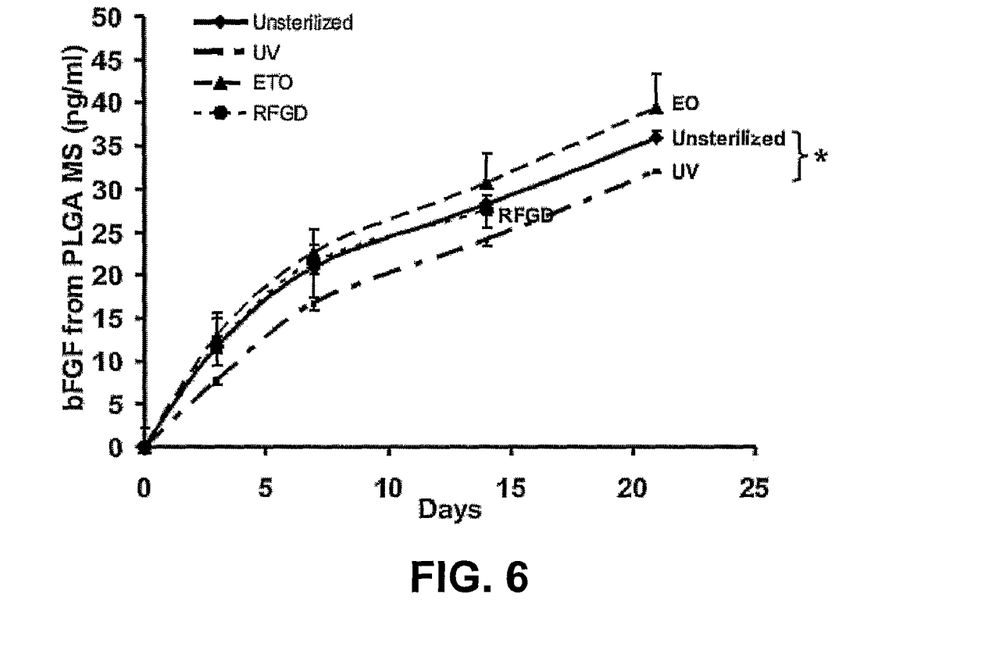
FIG. 6. illustrates release kinetics of bFGF from PLGA microspheres; ultra-violet light (UV) significantly altered the release rate of bFGF from PLGA microspheres up to 21 days (n=3, *$p<0.05$); no significant changes in release kinetics were observed after ethylene oxide (EO) gas or radio frequency glow discharge (RFGD) sterilizations; ethylene oxide is the most economically efficient and safe sterilization method for cytokine-encapsulating PLGA microspheres.
Figure 7:
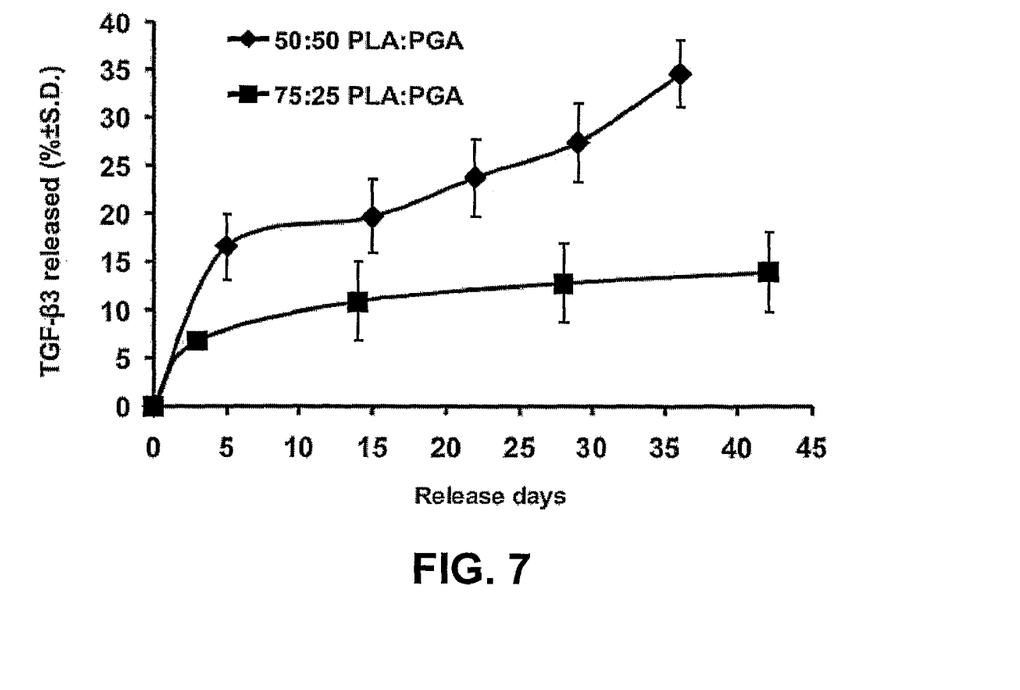
FIG. 7. shows release kinetics of TGFβ3 from PLGA microspheres in 1% BSA solution; TGFβ3 was released in a sustained fashion up to 36 and 42 days from 50:50 or 75:25 copolymer ratios PLGA microspheres respectively, as detected by ELISA; initial burst-like release was observed for both copolymer ratios, although the 50:50 PLA:PGA ratio yielded a more rapid release rate than the 75:25 PLA:PGA ratio.
Figure 8:
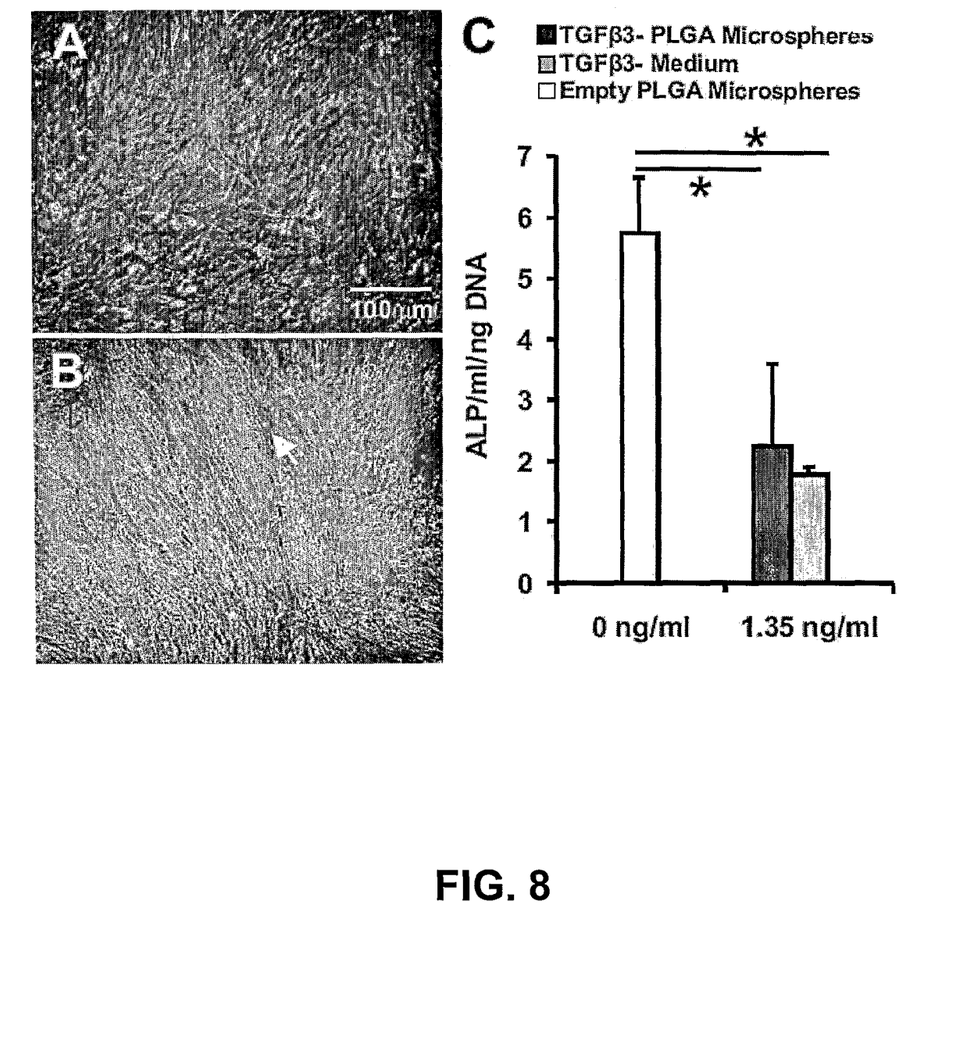
FIG. 8 shows alkaline phosphatase (ALP) activity of human mesenchymal stem cells (hMSCs) cultured with osteogenic supplemented medium for 7 days. A: ALP staining upon exposure to TGFβ3-free PLGA microspheres. B: ALP staining upon exposure to TGFβ3 released from PLGA microspheres; stain is limited to isolated regions as shown by a white arrow head; C: ALP activity of hMSCs cultured in osteogenic supplemented medium quantified by ALP reagent; significant decrease in staining was observed for hMSCs cultured in osteogenic supplemented medium in PLGA microsphere delivered TGFβ3, suggesting that TGFβ3 at 1.35 ng/ml inhibits early osteogenic differentiation of hMSCs in vitro (n=3, p<0.05). 10× magnification.

The bFGF release rate was significantly reduced after UV light sterilization in comparison to each of un-sterilized PLGA microspheres, EO or RFGD sterilization modalities (FIG. 6). This reduction in bFGF release rate upon UV treatment corroborated with the SEM observation of degrading surface structures of PLGA microspheres after UV sterilization (FIG. 5B). No statistically significant difference was found in the bFGF release rates of either EO- or RFGD-sterilized PLGA microsphere from un-sterilized controls (FIG. 6). Accordingly, ethylene oxide gas was chosen as the sterilization technique for TGFβ3 encapsulated PLGA microspheres in subsequent experiments due to lower cost and less damage to microsphere morphology.
TGFβ3 Release Kinetics TGFβ3 from PLGA microspheres was released up to the tested 36 and 42 days in vitro for both 50:50 and 75:25 co-polymer ratios of PLA:PGA, respectively (FIG. 7). The TGFβ3 entrapment yield was 0.68 ng/ml per mg of 75:25 PLGA microspheres and 0.24 ng/ml per mg of 50:50 PLGA microspheres. A burst-like release was observed for PLGA microspheres with either 50:50 or 75:25 copolymer ratios during the first week, followed by more gradual increases in release rate for the 75:25 polymer ratio (FIG. 7). More rapid release of TGFβ3 was obtained for the 50:50 copolymer ratio of PLA:PGA than the 75:25 PLA:PGA (FIG. 7), likely due to more rapid degradation rate of 50:50 PLGA. Approximately 8% of the encapsulated TGFβ3 by 75:25 PLGA was released within the first week, versus nearly 16% TGFβ3 release from 50:50 PLGA for the same time period. After 35 days, approximately 14% and 34% TGFβ3 was released from 75:25 and 50:50 copolymer ratios PLGA, respectively.
Inhibition of Osteogenic Differentiation of hMSCs Human MSC expressed a relatively high average alkaline phosphatase by Day 7 culture in osteogenic supplemented medium in vitro, as evidenced by both ALP staining and quantification using enzyme reagent (FIGS. 8A and 8C). ALP activity of hMSC cells exposed to TGFβ3 (1.35 ng/ml) released from PLGA microspheres by Day 7 culture in osteogenic supplemented medium was significantly inhibited as evidenced by not only reduced ALP staining (FIG. 8B), but also quantitative amount of ALP (FIG. 5C). The same-dose TGFβ3 (1.35 ng/ml) added directly to culture medium of hMSC (without microencapsulation) also yielded significantly less ALP activity than hMSC without exposure to exogenously delivered TGFβ3 (FIG. 5C). Moreover, the lack of statistically significant differences in ALP reductions between TGFβ3 added to cell culture medium and the same-dosed TGFβ3 released from PLGA microspheres (FIG. 5C) indicated that bioactive TGFβ3 was released from PLGA microspheres after microencapsulation and the subsequent EO sterilization.

Previous work has shown that TGFβ3 induces chondrogenic differentiation of mesenchymal stem cells at a much greater concentration (10 ng/ml) than reported herein (1.35 ng/ml). To rule out chondrogenesis by the present TGFβ3 dose up to 1.35 ng/ml, negative safranin-O staining of hMSC monolayer cultured with TGFβ3 loaded PLGA microspheres was observed.

Discussion

The findings of sustained release of TGFβ3 in PLGA microspheres is applicable to wound healing and tissue regeneration. Long-term delivery of TGFβ3 via controlled release approach regulates cell recruitment, proliferation and differentiation. TGFβ3 acts on cell metabolism via the Smad pathways to target gene transcription. The type I and type II dimeric TGFβ receptors capture TGFβ3 at cell surfaces and activate a cascade of Smad events, relaying the signal to cell nucleus. Sustained release enables prolonged delivery of cytokines in contrast to diffusion, inactivation and loss of bioactivity associated with injection or soaking cytokines in biomaterials. The presently identified TGFβ3 sustained release profiles from PLGA microspheres using 50:50 and 75:25 PLA:PGA ratios shows that the release rates of TGFβ3 from PLGA microspheres can be readily tailored towards specific degradation needs by modifying the ratio of PLA:PGA. The methyl group in PLA is responsible for its hydrophobic and slow degradation. PGA is crystalline and increases degradation times. Therefore, different ratios of PGA and PLA accommodate specific growth factor release rates. Although the initial burst release was lower than expected, the preparation of PLGA microspheres did not include techniques to prevent the burst. The encapsulation of TGFβ3 in PLGA microspheres is a novel approach, and relatively lower initial burst release may be attributed to specific growth factor-polymer interactions. This system for TGFβ3 via PLGA microspheres provides a mechanism for sustained long-term release.

The application of PLGA microspheres in drug delivery and regenerative medicine requires adequate preparation methods including appropriate sterilization techniques. The optimal sterilization technique should maintain the bioactivity and the predefined release kinetics of the encapsulated growth factors. The present demonstration that ultra-violet light induced significantly more surface damage of bFGF-encapsulated PLGA microspheres and reduced the rate of growth factor release than both ethylene oxide gas and radio frequency glow discharge, cautions against the use of UV light for PLGA microsphere sterilization. The reduced release rate may be attributed to polymer surface and/or bulk degradation during sterilization and consequent decreases in the amount of bFGF. Also, direct growth factor degradation due to light, may explain the decreases in bFGF release rate from UV sterilized PLGA microspheres. Surface degradation was observed subsequent to incubation in aqueous environment, suggestive of hydrolysis of the polymer structure.

Neither ethylene oxide gas nor radio frequency glow discharge significantly altered the release kinetics of bFGF from PLGA microspheres. Although sterilization using gamma irradiation is well documented, the equipment for gamma-irradiation sterilization may not be widely available in most laboratories. Accordingly, ethylene oxide is a logical choice for the sterilization of growth factor-encapsulating PLGA micro spheres.

The bioactivity of TGFβ3 released from PLGA microspheres is verified by a lack of statistically significant differences in ALP activity of osteogenic cells derived from human mesenchymal stem cells between microsphere-released TGFβ3 and the same-dose TGFβ3 added directly to cell culture.

The inhibitory effects of TGFβ3 on osteogenic differentiation of human mesenchymal stem cells are useful in several tissue engineering models. For example, undesirable ectopic bone formation occurs in approximately 28% of tissue-engineered rabbit tendon repairs from mesenchymal stem cells. Sustained release of TGFβ3 from PLGA microspheres, may help reduce the incidence of ectopic bone formation. Unintended osteogenic differentiation of mesenchymal stem cells may occur in articular cartilage tissue-engineering, and can be dealt with by the delivery of TGFβ3 in microspheres. At higher doses, TGFβ3 or TGFβ1 (typically 10 ng/ml) induces chondrogenic differentiation of mesenchymal stem cells.

Another tissue engineering use for sustained release of TGFβ3 is to inhibit osteoblast activity and to prevent premature ossification of cranial sutures, a pathological condition leading to craniosynostosis manifesting as skull deformities, seizure and blindness. Tissue-engineered cranial sutures, if applied to a craniosynostosis model, may suffer the same fate of premature ossification as pathologically synostosed cranial sutures. Previous approaches of TGFβ3 delivery may be further improved by a sustained release approach that enables more prolonged action and precise control of the encapsulated growth factor. In early osteogenesis differentiation of human mesenchymal stem cells in vitro can be inhibited by TGFβ3 in both encapsulated and un-encapsulated forms. Due to the mesenchymal tissue nature of patent cranial sutures, mesenchymal stem cells likely play a pivotal role in premature suture ossification.

Example 2

Titanium Implants

Smooth, commercially pure titanium implants were custom manufactured at the Medical Devices machine shop at the University of Illinois at Chicago. The implants were hollow cylindrical titanium rods measuring 4 mm×2 mm×6 mm (outer diameter×inner diameter×length). The implants also contained 4 cross-holes measuring 1 mm in diameter. The dimensions of the implants reflected those of common dental implants currently available on the market. Even though the implants were modeled from dental implants, this technology has orthopaedic applications.

Materials and Methods

Polylactic-co-glycolic acid (PLGA) is an FDA approved co-polymer that has been shown to be effective in controlled delivery of large biomolecules, such as growth factors. When processed correctly, PLGA can be made to form microspheres encapsulating biomolecules. PLGA microspheres were made in the laboratory that averaged 64±μm in diameter and encapsulating TGF-β1. PLGA microspheres can also be made using varying ratios of PLA:PGA to vary the release rate of encapsulated molecules. An in vitro release study of 50:50 PLGA microspheres encapsulating TGF-β1 showed that the TGF-β1 is released in a quick burst of approximately 0.2±0.05 ng in 3 days and sustains release up to 4 weeks.

CITATIONS

1. Hosokawa, R., et al, *J Dent. Res.*, 82, 558, 2003.
2. Levine, J. H., et al, *Am. J Pathol.*, 143, 368, 1993.
3. Kohama, K., et al, *J Dent. Res.*, 81, 688, 2002.
4. Cohen, M. M., Jr., et al, *J Craniofac. Genet. Dev. Biol.*, 20, 19, 2000.
5. Opperman, L. A., et al, *Orthod. Craniofac. Res.*, 5, 5, 2002.
6. Greenwald, J. A., et al, *J Bone Miner. Res.*, 15, 2413, 2000.
7. Richman, J. M., Kollar, E. J., et al, *Am. J Anat.*, 175, 493, 1986.
8. Gato, A., et al, *Dev. Biol.*, 250, 393, 2002.
9. Copland, I. B., et al, *Placenta*, 23, 311, 2002.
10. Kay, E. P., et al, *Curr. Eye Res.*, 17, 286, 1998.
11. Kay, E. P., et al, *Invest Ophthalmol. Vis. Sci.*, 39, 481, 1998.
12. Hirshberg, J., et al, *Adv. Skin Wound. Care*, 14, 91, 2001.
13. Opperman, L. A., et al, *Anat. Rec.*, 267, 120, 2002.
14. Chong S L., et al, *Anat. Rec. A Discov. Mol. Cell. Evol. Biol.*, 274, 962, 2003.
15. Parker J A, et al, *Tissue Eng.* 8, 853, 2002.
16. Garcia-Fuentes M, et al, *J Colloid Interface Sci.* 15, 590, 2005.
17. Prabaharan M, and Mano J F., et al, *Drug Deliv.* 12, 41, 2005.
18. Muvaffak A, et al, *J Biomed Mater Res B Appl Biomater.* 15, 295, 2004.
19. Ksander G A, et al, *Ann Surg.* 211, 288, 1990.
20. Pandit A, et al, *J Invest Surg.* 12, 89, 1999.
21. Midy V, et al, *J Biomed Mater Res.* 5, 405, 1998.
22. Gombotz W R, et al, *J Appl Biomater.* 5, 141, 1994.
23. Nicoll S B, et al, *Biomaterials.* 18, 853, 1997.
24. Holland, T. A., Mikos, A. G., Control Release, 86, 1, 2003.
25. Lu, L., et al, *J Bone Joint Surg. Am.*, 83-A Suppl 1, S82-S91, 2001.
26. Ding, A. G., Schwendeman, S. P., J Pharm. Sci., 93, 322, 2004.
27. Cohen, S., et al, *Pharm. Res.*, 8, 713, 1991.
28. Woo, B. H., et al, *Pharm. Res.*, 18, 1747, 2001.
29. Oldham, J. B., et al, *J Biomech. Eng*, 122, 289, 2000.
30. Carrascosa, C., et al, *Biomaterials*, 25, 707, 2004.
31. Jiang, W., et al, *Adv. Drug Deliv. Rev.*, 57, 391, 2005.
32. Cleland J L, et al, *J. Control Release.* 72, 13, 2001.
33. Kojima K, et al, *J. Thorac Cardiovasc Surg.* 128, 147, 2004.
34. Peter S J, et al, *J Biomed Mater Res.* 5, 452, 2000.
35. Aubert-Pouessel A, et al, *J Control Release.* 95, 463, 2004.
36. Mittal S, et al, *Neuroreport.* 5, 2577, 1994.
37. Opperman L A, et al, *J Bone Miner Res.* 12, 301, 1997.
38. Poisson E, et al, *Cleft Palate Craniofac J.* 41, 392, 2004.
39. Wei G, et al, *Biomaterials* 25, 345, 2004.
40. Ruan, G., et al., J Control Release, 84, 151, 2002.
41. Cleek R L, et al., J Biomed Mater Res. 35, 525, 1997.
42. Alhadlaq, A., et al, *Ann. Biomed. Eng*, 32, 911, 2004.
43. Alhadlaq, A., and Mao, J. J., *Stem Cells Dev.*, 13, 436, 2004.
44. Alhadlaq, A., Mao, J. J., *J Dent. Res.*, 82, 951, 2003.
45. Ferguson, M. W., O'Kane, S., Philos. *Trans. R. Soc. Lond B Biol. Sci.*, 359, 839, 2004.
46. Chin, G. S., et al, *Plast. Reconstr. Surg.*, 108, 423, 2001.
47. Schiller, M., et al, *J Dermatol Sci.*, 35, 83, 2004.
48. Verrecchia, F., and Mauviel, A., J Invest Dermatol, 118, 211, 2002.
49. Ratner, B. D, et al, New York: Academic Press, 1996.
50. Elisseeff J, et al, *J Orthop Res.* 19, 1098, 2001.
51. Baroli B, et al, *J Pharm Sci.* 92, 1186, 2003.
52. Lewis K J, et al, *J Drug Target.* 5, 291, 1998.
53. Martinez-Sancho, C., et al, *J Control Release*, 99, 41, 2004.
54. Carrascosa, C., et al, *J Biomater. Appl.*, 18, 95, 2003.
55. Harris, M. T., et al, *J Orthop. Res.*, 22, 998, 2004.
56. Mao, J. J., *J Dent. Res.*, 81, 810, 2002.
57. Hong, L., Mao, J. J., *J Dent. Res.*, 83, 751, 2004.
58. Mao, J. J., Nah, H. D., *Am. J Orthod. Dentofacial Orthop.*, 125, 676, 2004.
59. Kojima K, et al, *J Thorac. Cardiovasc. Surg.* 128, 147, 2004.

What is claimed is:

1. A non-collapsible implant for bone, the implant comprising a hollow core, porous side walls, and a foraminous biocompatible material wherein a biological matrix or scaffold is stored within the hollow core, and includes a biological or chemical agent(s) encapsulated within microspheres that are released by controlled release technology temporally and spatially, accelerating bone healing.

2. The implant of claim 1 wherein the biocompatible material consists of monomers or polymers.

3. The implant of claim 1 wherein the biocompatible material is one or more metals selected from the group consisting of stainless steel, titanium, and metal alloys.

4. The implant of claim 1 further defined as having a cross section that is cylindrical, square, rectangular or an irregular shape depending on the anatomic location of the bone.

5. The implant of claim 1 wherein the biological or chemical agent(s) move in and out of the porous side walls.

6. The implant of claim 1 wherein the agent is encapsulated by a chemical polymer or monomer that is selected from the group consisting of collagen, gelatin, polylactic acid, polyglycolic acid, polyethylene glycol and a polyethylene glycol or a mixture thereof.

7. The implant of claim 1 wherein said encapsulated biological agent is a growth factor.

8. The implant of claim 1 wherein the microspheres are inserted into a biological matrix or scaffold comprising collagen.

9. The implant of claim 8 wherein the biological matrix further comprises an osteogenic agent.

10. The implant of claim 9 wherein the osteogenic agent is dexamethasone.

11. The implant of claim 8 wherein the biological matrix further comprises a nutrient medium.

12. The implant of claim 1, wherein the microspheres are comprised of a hydrogel.

13. The implant of claim 12, wherein the microspheres are inserted into a biological matrix or scaffold, which may include a natural material selected from the group consisting of: alginate, sponge, chitosan, coral, agarose, fibrin, collagen, bone, silicone, cartilage, hydroxyapatite, calcium phosphate, hydrogel and mixtures thereof.

14. The implant of claim 13, wherein the biological matrix or scaffold is a collagen sponge.

15. A non-collapsible implant for bone, the implant comprising a hollow core, non-expandable porous side walls, and a biocompatible material, wherein a biological matrix or scaffold is stored within the hollow core and includes a biological or chemical agent(s) encapsulated within microspheres, wherein the microspheres are inserted into biological matrix or scaffold, and the biological or chemical agent(s) are released through the porous side walls by controlled release technology temporally and spatially, accelerating bone healing.

16. The implant of claim 15, wherein the biological matrix or scaffold is a collagen sponge.

* * * * *